US009628897B2

(12) United States Patent
Fletcher et al.

(10) Patent No.: US 9,628,897 B2
(45) Date of Patent: Apr. 18, 2017

(54) ADAPTIVE FREQUENCY RESPONSE, ADAPTIVE AUTOMATIC LEVEL CONTROL AND HANDLING RADIO COMMUNICATIONS FOR A HEARING PROTECTOR

(71) Applicant: 3M INNOVATIVE PROPERTIES COMPANY, St. Paul, MN (US)

(72) Inventors: Douglas D. Fletcher, Woodbury, MN (US); Oscar M. Hemberg, Dalaro (SE); Eric O. Hemberg, Shatin (HK)

(73) Assignee: 3M Innovative Properties Company, St. Paul, MN (US)

( * ) Notice: Subject to any disclaimer, the term of this patent is extended or adjusted under 35 U.S.C. 154(b) by 86 days.

(21) Appl. No.: 14/524,014

(22) Filed: Oct. 27, 2014

(65) Prior Publication Data

US 2015/0117660 A1 Apr. 30, 2015

Related U.S. Application Data

(60) Provisional application No. 61/896,537, filed on Oct. 28, 2013, provisional application No. 61/993,920, filed on May 15, 2014.

(51) Int. Cl.
*A61F 11/06* (2006.01)
*H04R 1/10* (2006.01)
*G10K 11/178* (2006.01)
*A61F 11/14* (2006.01)

(52) U.S. Cl.
CPC ......... *H04R 1/1083* (2013.01); *G10K 11/178* (2013.01); *A61F 2011/145* (2013.01); *G10K 2210/1081* (2013.01)

(58) Field of Classification Search
USPC ............ 381/56–59, 71.1, 71.6, 71.11, 71.13, 381/71.14, 72, 73.1, 94.1–94.8, 98, 104, 381/107, 109, 120, 122; 704/226, 704/E21.002, E21.014; 375/346; 379/392.01
See application file for complete search history.

(56) References Cited

U.S. PATENT DOCUMENTS

| 3,908,168 | A | 9/1975 | Mcmahon |
| 4,928,311 | A | 5/1990 | Trompler |
| 5,091,954 | A | 2/1992 | Sasaki |
| 5,113,428 | A | 5/1992 | Fitzgerald |

(Continued)

FOREIGN PATENT DOCUMENTS

| GB | 2456297 | 7/2009 |
| WO | WO 96/08001 | 3/1996 |

OTHER PUBLICATIONS

PCT International Search Report for PCT/US2014/062353 mailed on Jan. 15, 2015, 3 pages.

(Continued)

*Primary Examiner* — Vivian Chin
*Assistant Examiner* — Friedrich W Fahnert

(57) ABSTRACT

An hearing protection device is provided. The hearing protection device can include a speaker to relay sounds, such as conversations, to the user of the hearing protection. The hearing protection device can include an electronics package that can filter out undesirable sounds, such as to improve the user's ability to hear conversations around them while still protecting the user's ears.

20 Claims, 5 Drawing Sheets

(56) References Cited

U.S. PATENT DOCUMENTS

| | | |
|---|---|---|
| 5,182,774 A | 1/1993 | Bourk |
| 5,285,502 A | 2/1994 | Walton |
| 5,369,711 A | 11/1994 | Williamson |
| 5,485,522 A | 1/1996 | Soelve |
| 5,550,923 A | 8/1996 | Hotvet |
| 5,675,658 A | 10/1997 | Brittain |
| 6,741,707 B2 * | 5/2004 | Ray ............... G10K 11/178 381/71.11 |
| 7,010,118 B2 | 3/2006 | Etter |
| 7,242,765 B2 | 7/2007 | Hairston |
| 7,317,802 B2 | 1/2008 | Wurtz |
| 7,376,557 B2 | 5/2008 | Specht |
| 7,908,139 B2 | 3/2011 | Jang |
| 7,983,425 B2 | 7/2011 | Luo |
| 8,073,145 B2 | 12/2011 | Kondo |
| 8,111,839 B2 * | 2/2012 | Goldstein ........... H04R 1/1091 381/1 |
| 8,199,923 B2 | 6/2012 | Christoph |
| 8,320,591 B1 | 11/2012 | Wurtz |
| 8,472,637 B2 | 6/2013 | Carreras |
| 2002/0184013 A1 | 12/2002 | Walker |
| 2004/0247060 A1 * | 12/2004 | Shibuya ............. G10L 21/0208 375/346 |
| 2006/0098826 A1 | 5/2006 | Merline et al. |
| 2006/0262938 A1 | 11/2006 | Gauger, Jr. et al. |
| 2007/0154027 A1 * | 7/2007 | Werner ............. G10K 11/1788 381/71.1 |
| 2008/0077403 A1 | 3/2008 | Hayakawa |
| 2008/0144842 A1 * | 6/2008 | Goldstein ............. A61B 5/121 381/56 |
| 2009/0262969 A1 | 10/2009 | Short |
| 2010/0061564 A1 | 3/2010 | Clemow et al. |
| 2010/0260345 A1 * | 10/2010 | Shridhar ............... G10K 11/178 381/71.1 |
| 2011/0096942 A1 * | 4/2011 | Thyssen ............... G10L 21/0208 381/94.1 |
| 2011/0280411 A1 | 11/2011 | Cheah et al. |
| 2012/0014532 A1 | 1/2012 | Kimura |
| 2012/0170766 A1 | 7/2012 | Alves |
| 2012/0250873 A1 | 10/2012 | Bakalos |
| 2013/0060567 A1 | 3/2013 | Konchitsky |
| 2013/0083939 A1 | 4/2013 | Fellers |
| 2013/0094657 A1 * | 4/2013 | Brammer ........... G10K 11/1788 381/71.6 |
| 2013/0094658 A1 * | 4/2013 | Holter ................. H04R 1/1083 381/72 |
| 2013/0101129 A1 | 4/2013 | Christoph |
| 2013/0108068 A1 | 5/2013 | Poulsen |
| 2013/0163775 A1 | 6/2013 | Yamkovoy |
| 2014/0177868 A1 * | 6/2014 | Jensen ................... H04R 3/002 381/94.7 |
| 2014/0294191 A1 * | 10/2014 | Parkins ................. A61F 11/06 381/72 |
| 2015/0010158 A1 * | 1/2015 | Broadley ............... H04R 29/00 381/58 |

OTHER PUBLICATIONS

Unknown, "Peltor Sound-Trap", AearoPELTOR, Product User Manual, Produced by LGSE at least as early at 1998., 2 pages.

* cited by examiner

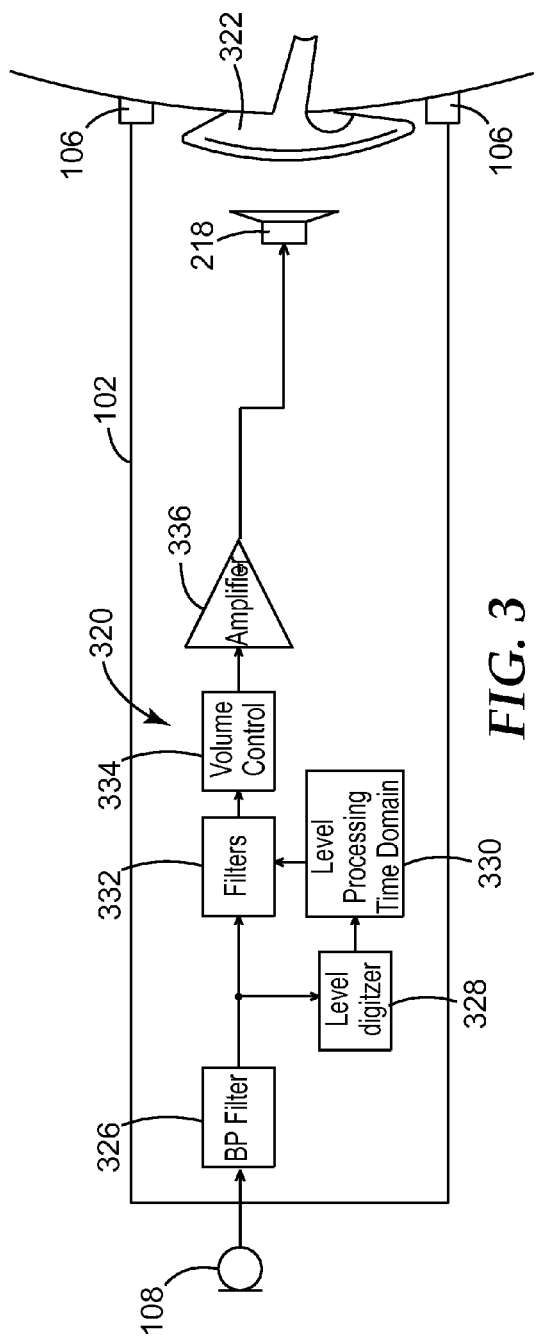
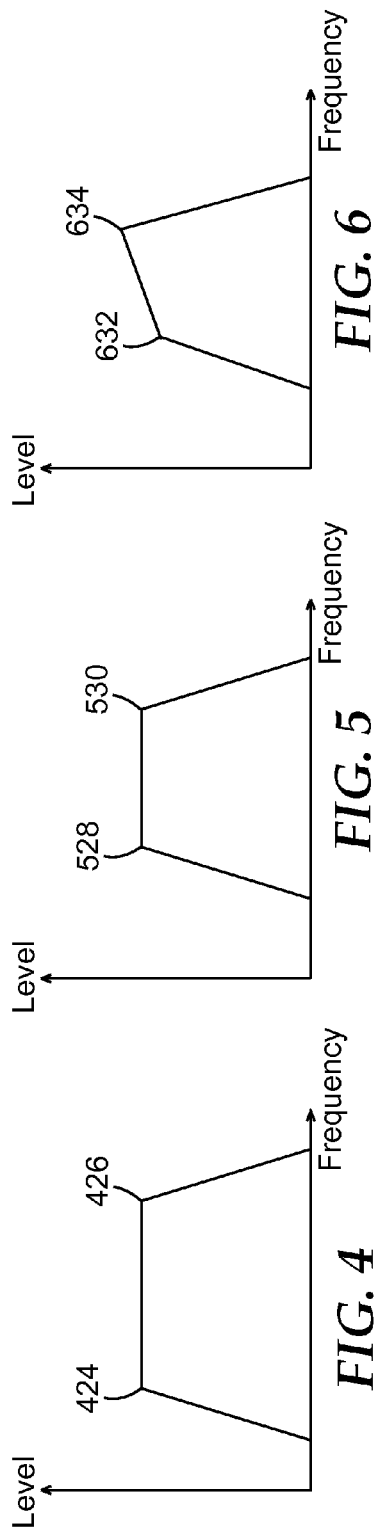
FIG. 3
FIG. 4
FIG. 5
FIG. 6

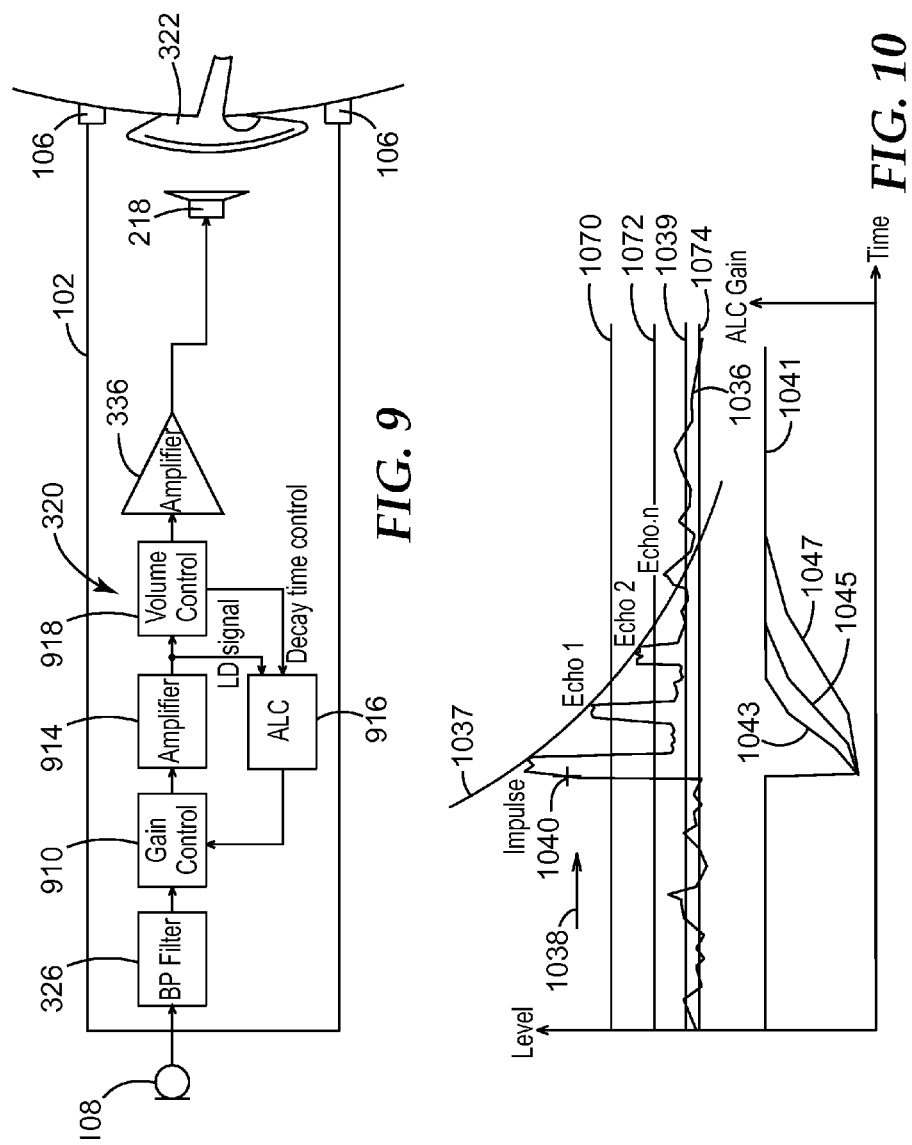

ADAPTIVE FREQUENCY RESPONSE, ADAPTIVE AUTOMATIC LEVEL CONTROL AND HANDLING RADIO COMMUNICATIONS FOR A HEARING PROTECTOR

BACKGROUND

People frequently wear hearing protection when they are in loud or noisy environments. Hearing protection can reduce the amount of noise the user's ears are exposed to. In some cases the user might want to hear some noises, such as a conversations or commands from people around them. If the user is wearing hearing protection, hearing these desirable noises can be difficult or impossible. Therefore, there is a need to allow the user of hearing protection to still be able to hear some external noises, while still reducing the loud or undesirable noises.

SUMMARY

Sound external to a hearing protection headset can be input by one or more microphones on the headset. The ambient external sound or background noises can be monitored, analyzed and filtered so that a user of the headset can better hear human voices.

In one example, an apparatus for hearing protection, includes a microphone disposed on the apparatus. The microphone is configured to pick up an input sound wave from the environment and to convert the input sound wave to an incoming signal. The apparatus also includes a processor that is configured to apply a band pass filter to the incoming signal to create an output signal. The apparatus can further include a speaker disposed on the apparatus. The speaker is configured to produce the output from the processor. The band pass filter, applied by the processor, is selected from a plurality of band pass filters. The selection of the band pass filter is based on an average amplitude of the incoming sound wave. At least one of the band pass filters for larger amplitudes is more narrowly focused on a selected range of frequencies than at least one of the band pass filters for smaller amplitudes.

In one example, an apparatus for hearing protection, includes a microphone disposed on the apparatus and configured to pick up an input sound wave from the environment and convert the input sound wave to an incoming signal. The apparatus also includes a processor, configured to apply a band pass filter to the incoming signal wherein frequencies of an output signal of the band pass filter vary depending on an amplitude of the incoming signal. The process is also configured to perform one of two steps. The first option is detecting an impulse noise when the amplitude of the input surpasses an impulse detection threshold, when an impulse noise is detected the output is suppressed for a period of time, wherein the suppression period of time depends on a volume level setting selected by the user. The second option is keeping the gain of an automatic level controller constant when the audio device input is below a gate threshold, and the output reduced to an ALC maximum level when the output would otherwise have been above the ALC maximum level. The apparatus also includes a speaker disposed on the apparatus, the speaker configured to produce the output from the processor.

In one example, an apparatus for hearing protection, includes means for picking up an input sound wave from an environment, means for converting the input sound wave to an incoming signal, means for selecting a band pass filter from a plurality of band pass filters, means for applying the selected band pass filter to the incoming signal to create an output, and means for converting the output to an output sound wave. The band pass filter is selected from a plurality of band pass filters based on an average amplitude of the incoming sound wave. The band pass filters for larger amplitudes are more narrowly focused on a range of frequencies.

BRIEF DESCRIPTION OF THE DRAWINGS

The invention may be more completely understood in connection with the following drawings, in which:

FIG. 3 is a block diagram of a process, according to an embodiment.

FIG. 4 is a graph of audio filter behavior, according to an embodiment.

FIG. 5 is a graph of audio filter behavior, according to an embodiment.

FIG. 6 is a graph of audio filter behavior, according to an embodiment.

FIG. 9 is a block diagram of a process, according to an embodiment.

FIG. 10 is a graph of audio filter behavior, according to an embodiment.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Figure 1:
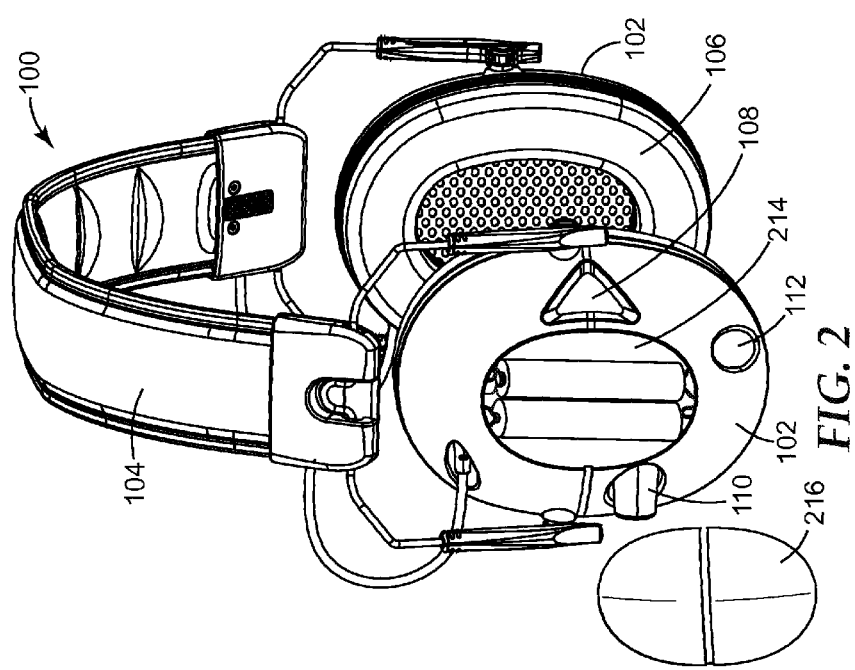
FIG. 1 is a perspective view of the headset, according to an embodiment.

FIG. 1 is a perspective view of a headset 100. In an embodiment, the headset 100 can include an ear cup 102 and a headband 104. The headset 100 can include two ear cups 102. The headband 104 can couple a first ear cup 102 with a second ear cup 102. The headband 104 can be arced, such as to extend over the top of a user's head while the headset 100 is in use. The headband 104 can be flexible, such as to allow the user to spread the first ear cup 102 from the second ear cup 102 when the user is putting on the headset 100. The headband 104 can include padding, such as to at least partially conform to the user's head and increase the user's comfort.

The ear cups 102 can be configured to fit at least partially around a user's ear, and be disposed on the side of a user's head while in use. The ear cup 102 can define a cavity. The cavity can be configured for a user's ear, a human ear, to fit within, while the user is wearing the headset 100. The ear cup 102 can include a seal ring 106. The seal ring 106 can be ring shaped, such as to extend around the user's ear. The seal ring 106 can be flexible and able to conform to the user's head. The seal ring 106 can provide a seal between the ear cup 102 and the user's head, such as to reduce the amount of noise or sound waves that reach the user's ear, thereby at least partially protecting the user's ear from external noises. The seal ring 106 can include leather, cloth, rubber, plastic, or a polymer, such as polyurethane.

In an alternative embodiment, the headset can include a housing that is configured to fit at least partially within the outer portion of a user's ear, such as within a portion of the auricle or pinna. In an embodiment, the headset can include two housings, such as a right housing configured to fit at least partially within the user right ear and a left housing configured to fit at least partially within the user left ear. In an embodiment, the right housing and left housing can be substantially identical, such that the right housing can be used in association with the left ear and the left housing can be used in association with the right ear.

The headset 100 can include a microphone 108. In one embodiment, one or both of the ear cups 102 can include a microphone 108. In an embodiment, there is one microphone 108 on each of two ear cups 102. In an embodiment, there can be more than one microphone 108 on one or both of the ear cups 102. In one embodiment, one or more microphones 108 are located at other locations on the headset 100. The microphone 108 can be disposed on the outside surface of the ear cup 102 opposite the cavity. The microphone 108 can pick up sound and noise from the surrounding environment. The microphone 108 can be inset, such that the microphone 108 does not extend past the outer surface of the ear cup 102. In an embodiment with two ear cups 102, each ear cup 102 can include a microphone 108. In another embodiment with two ear cups 102, only one ear cup 102 includes a microphone 108. In another embodiment with two ear cups 102, one microphone 108 is positioned on a headband portion. The noises and sounds picked up by the microphone 108 can be relayed to the user through a speaker in the cavity of the ear cup 102.

One of the ear cups 102 can include a knob 110. The user can rotate the knob 110 to control the electronics of the headset 100, such as to turn the electronics "ON" or "OFF", or to increase or decrease the volume from the speakers in the ear cups 102.

The ear cups 102 can include an input connection 112. The input connection 112 can allow a user to connect an external audio device into the headset 100, such as an AM/FM radio, a two-way radio, an MP3 player, a cell phone, or the like. The user can hear the external audio device through the one or more speakers disposed in the ear cups 102. In an embodiment, the input connection 112 can accommodate a 3.5 mm audio input. In an embodiment, the external audio device can be connected to the headset 100 through a wireless connection, such as Bluetooth connection. In an embodiment, the external audio device can be built in or integral with the headset 100.

Despite the presence of the ear cups forming a seal against the user's head, some sound waves will travel through the bone and open spaces of the user's skull to reach the ear canal, such as through the cranium, mouth or nose. Some sound waves come through the sealing rings, the ear cups, or other physical mechanisms. The level of sound traveling through these other pathways, referred to a leakage sound, is not reduced by hearing protection worn over or in the ears, such as the headset 100 or ear plugs. So, a portion of the sound will be heard as leakage sound conducted through these other pathways, even if sufficient hearing protection is worn so that the same sound is not heard as sound conducted through the environment to the ear. Around 40 dB is the maximum reduction that can be achieved assuming a perfect hearing protector, because leakage sound through the skull will still reach the ear canal. If a sound is above 40 dB, it will reach the ear canal even if hearing protection is worn. A typical decibel level of a gunshot is about 149 dB (typically between 140 dB and 170 dB).

A generally accepted safe level of sound to reach the ears is an average of about 85 dB over 8 hours, though different sound levels are considered safe by government, medical or other entities in different contexts and averaged over different time periods, such as 80 dB, 90 dB or 100 dB. Similarly, a generally accepted safe level of sound to reach the ears is an instantaneous level of 114 dB, though different levels are also considered safe in different contexts and by different entities, such as 100 dB, 110 dB, or 120 dB. The occurrence of sound leakage can be accounted for when determining the level of sound to produce using the speakers in the ear cups of headset 100. For example, a portion of the safe sound level can be allocated to be received as leakage, and then sound produced by the speakers will allocated the other portion of the safe sound level. In one example, half of the safe sound level is allocated to be received as leakage. The decibel scale is a logarithmic scale, so every 3 dB drop in sound level reduces the incoming noise by half. Using the example of a safe sound level of 85 dB and a leakage allocation of 50%, one option is for one half (82 dB) to be allocated to leakage and for a maximum of the other half (82 dB) to be provided by the speakers. In this example, the output of the speakers will be limited to 82 dB.

Figure 2:
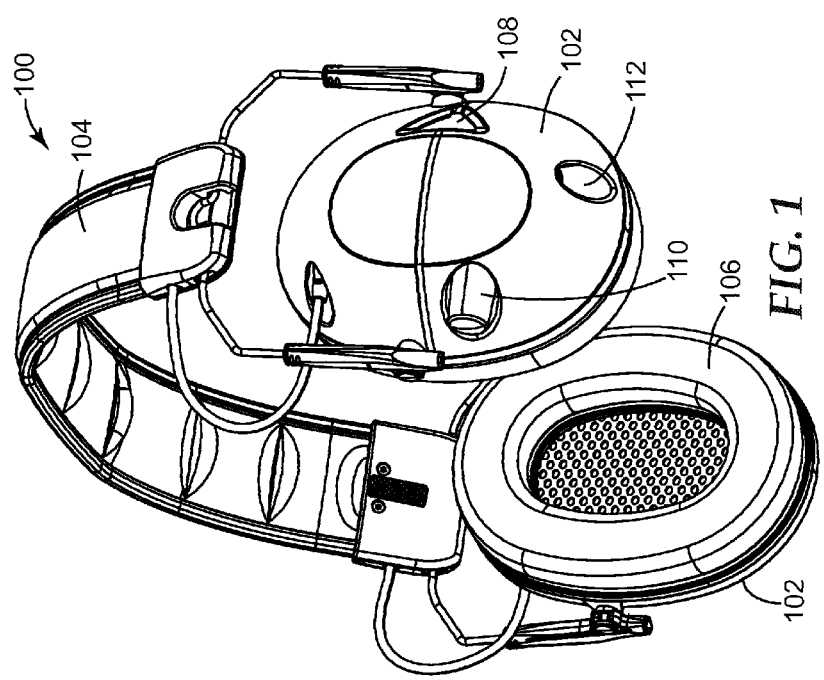
FIG. 2 is a perspective view of the headset, according to an embodiment.

A perspective view of the headset 100 is shown in FIG. 2, from a different perspective angle than what is shown in FIG. 1. The ear cups 102 can include a battery compartment 214. The battery compartment 214 can house one or more batteries. The batteries can be used to power the electronic components of the headset 100. In an embodiment, a plurality of AAA batteries can be disposed within the battery compartment 214. In an embodiment, the headset 100 can use lithium ion batteries, AA batteries, rechargeable batteries, non-rechargeable batteries, or a combination of these different batteries. A battery door 216 can at least partially enclose the battery compartment 214. The battery door 216 can be configured to be removed from the headset 100 when access to the batteries are desired, such as to replace the batteries.

Each ear cup 102 can include a speaker 218. The speaker 218 can produce an output, such as a sound wave. Incoming sound and noise picked up by each microphone 108 can be processed, such as to eliminate at least some of the noise and produce an output through the speaker 218. As used herein, the term sound refers to desirable audio information while the term noise refers to undesirable audio information. The speaker 218 can provide sound to the user, such as desirable audio. Desirable audio can include conversations, commands, warnings or other communications, such as communications between two people. The input from each microphone can be processed to eliminate at least some of the noise, such as undesirable noises. Undesirable noises can include mechanical noises, noises from ventilation systems, distant conversations, impulse noises, grinding, squeaking, engine noises, gun shots, explosions and the other similar noises.

The speaker 218 can relay sounds from the surrounding environment picked up by the microphone 108. The speaker 218 can relay sounds from an external audio device connected from the input connection 112. The output from the speaker 218 can be limited to a maximum output level, such as to protect the user's ears. In different embodiments, the maximum output level from the speaker 218 due to sound from the microphone can be at least 80 dB(A), not more than 90 dB(A), at least 70 dB(A), not more than 100 dB(A), and combinations of these constraints. In an embodiment, the output from the speaker 218 is limited to 82 dB(A) when the ambient sound level is less than 106 dB(A), regardless of how high the user has the volume turned up. In an embodiment, the output from the speaker 218 is limited to 85 dB(A) when the ambient sound level is less than 106 dB(A), regardless of how high the user has the volume turned up. In an embodiment, the output from the speaker 218 is limited to 82 dB(A), regardless of how high the user has the volume turned up. In an embodiment, the output from the speaker 218 is limited to 85 dB(A), regardless of how high the user has the volume turned up. In an embodiment, the output from the speaker 218 can be limited to 82 dB(A) when an external audio device is connected to the input connection 112. The sounds picked up by the microphone 108 can be processed before they are produced as output from the speaker 218. The processing can increase the quality or clarity of what the user hears, such as by reducing background noise, suppressing impulse noises or keeping an input level constant. In one embodiment where each of two ear cups 102 has a microphone 108, the incoming sound and noise is processed by a single processor. In another embodiment where each of the two ear cups 102 has a microphone 108, the incoming sound and noise is processed by separate processors applying the same algorithms.

In another example, a hearing protector having one or more of the processing functions as described herein uses an in-ear structure rather than an over-the-ear, cup structure. In such an example, an ear plug structure can be used to reduce the sound waves reaching the inner ear. A speaker can be located on a portion of the in-ear structure that faces the inner ear, and one or more microphones are located on a portion of the in-ear structure that faces the user's environment.

The individual features described herein can be present in various embodiments. Also combinations of the individual features described herein can be present in various embodiments. In an embodiment, a headset 100 can include an adaptive frequency response. In an embodiment, a headset 100 can include adaptive automatic level control decay/hold/release timing. In an embodiment, a headset 100 can include a gated ALC for external input. In an embodiment, a headset 100 can include an adaptive frequency response and adaptive automatic level control decay/hold/release timing. In an embodiment, a headset 100 can include an adaptive frequency response and a gated ALC for external input. In an embodiment, a headset 100 can include adaptive automatic level control decay/hold/release timing and a gated ALC for external input. In an embodiment, a headset 100 can include an adaptive frequency response, adaptive automatic level control decay/hold/release timing, and a gated ALC for external input.

Adaptive Frequency Response

Noises and sounds external to the headset 100 can be input by the microphone 108. The external noises and sounds can be continuously processed by a first algorithm running on a microprocessor. The first algorithm can analyze the external noise and sounds, such as to determine the level or amplitude of the external noise and sound. After analyzing the external noise and sound the first algorithm can apply one of several digital filters to the incoming sounds to reduce the external noise. The filters can progressively focus on the frequencies of human voices as the amplitude of the external noise and sound increases. Reducing the bandwidth or focusing on the frequencies of human voices can improve the voice to noise ratio and improve the speech intelligibility of verbal commands and conversations in the presence of external noise.

Sounds can be picked up by the microphone and relayed to the user through the speaker. The headset 100 can include an electronics package. The electronics package can apply a first algorithm to the sounds picked up by the microphone. FIG. 3 shows a block diagram of the electronics package 320, according to an embodiment. The electronics package 320 can be disposed of within an ear cup 102. In an embodiment, each ear cup 102 has an electronics package 320 disposed within. In an embodiment, only one ear cup 102 has an electronics package 320 disposed within, and the electronics package is in communication with the other ear cup, such as via a wire that passes through the headband to the ear cup on the opposite side of the headset. The electronics package 320 can include an initial band pass filter 326, a level digitizer 328, a level processor 330, a gain controller 332, a volume control 334, and an amplifier 336.

In general, the headset 100 can reduce the amount of sound that user hears, such as by providing a seal around the ear cups 102 and the user's head. In some environments a user might desire to hear more of the surrounding environment than the user is able to hear, because of the seal between the ear cups 102 and the user's head. The microphone 108 can pick up sounds from the surrounding environment and relay them to a user's ear 322, such as through speaker 218.

The electronics package 320 can help improve the quality of the sounds relayed to the user, such as by decreasing undesirable sounds, or increasing desirable sounds. The electronics package 320 can convert an analog input to a digital signal. The electronics package 320 can decrease or at least partially filter out background noises. The electronics package 320 can focus the output of the speaker to a desirable frequency, such as the frequency ranges of a human voice.

In an embodiment, the headset 100 can be used in a loud environment, such as a shooting range. The user can wear the headset 100 to protect his or her ears from the loud noises. The sound picked up by the microphone 108 can be processed by the electronics package 320, such as to decrease or at least partially filter out the undesirable or loud noise and increase or amplify the desirable noises. In various embodiments, the headset 100 can include two microphones 108, such as one on each ear cup. In one embodiment, the input from each microphone is processed by an electronics package 320 and then provided to the speaker associated with that microphone. So, the input from the right microphone is processed by an electronics package and provided to the right speaker, while the input from the left microphone is processed by an electronics package 320 and provided to the right speaker. In another embodiment, the input processed by the electronics package 320 can be an average of the two microphones 108. The electronics package 320 can include a noise detector and a band pass filter. In an embodiment, the electronics package 320 can include a plurality of band pass filters. The algorithm can analyze the external noise and apply one of several appropriate band pass filters. The band pass filter used to filter the input from the microphone can be determined based on the sound level of the input from the microphone. The band pass filter can be selected based on an average amplitude.

The average amplitude used to select the band pass filter can be determined in a number of different ways. In an embodiment, the average amplitude is an average of the input from each of the two or more microphones. For example, the average amplitude can be an average of the input from a first microphone disposed on a first ear cup and a second microphone disposed on a second ear cup. In an embodiment, each input from a microphone can be root mean squared and then averaged with other root mean squared inputs from other microphones. In an alternative embodiment, input from each of the microphones can be averaged and then root mean squared. In an alternative embodiment, the inputs from the microphones can be combined, such as by setting the output as the maximum of the inputs.

In an embodiment, the average amplitude for selecting the band pass filter can be time averaged, such as to avoid fast changes of filters. In an embodiment, the electronics package 320 can include adding hysteresis, such as to avoid rapidly switching between filters even with time averaging. In an embodiment, the electronics package can select one of three band pass filters to apply to the input from the microphone. In an embodiment, the electronics package can select one of five band-pass filters to apply to the input from the microphone. Other numbers of band pass filters that the band pass filter is selected from are possible.

In an embodiment, a first band pass filter can be applied when the level of the incoming sound is less than a first threshold. A second band pass filter can be applied when the incoming sound is greater than the first threshold, but lower than a second threshold. A third band pass filter can be applied when the incoming sound is greater than the second threshold. In an embodiment, the first threshold can be at 85 dB(A). In an embodiment, the second threshold can be at 100 dB(A). In an alternative embodiment, the first threshold can be 65 dB(A) and the second threshold can be 80 dB(A).

In an embodiment, a single variable filter can be included. The single variable filter can vary the frequencies that are filtered based on the amplitude of the input. In this embodiment, the filter can increasingly focus on narrower frequency ranges close to the typical frequency ranges of the human voice, as the amplitude of the input increases.

FIGS. 4-6 show the output level on the vertical axis and the frequency of the output on the horizontal axis for each of three different band pass filters. Each of the band pass filters can focus on desirable frequencies, such as a range of frequencies that includes human voices. As shown in FIGS. 4-6, the first band pass filter (shown in FIG. 4) can focus on a wider range of frequencies than the third band pass filter (shown in FIG. 6).

FIG. 4 shows a representation of the first band pass filter that can be applied when the level of the sound is below the first threshold. The first band pass filter can filter out frequencies below the first low frequency 424 and above the first high frequency 426. The frequencies between the first low frequency 424 and the first high frequency 426 can include the common frequencies for human voices, such as if the user desires to hear other people's voice. In an embodiment, the first low frequency 424 can be 100 Hz. In an embodiment, the first high frequency 426 can be 10 KHz.

FIG. 5 shows a representation of the second band pass filter that can be applied when the level of the sound is above the first threshold and below the second threshold. The second band pass filter can filter out frequencies below the second low frequency 526 and above the second high frequency 530. The frequencies between the second low frequency 528 and the second high frequency 530 can include the common frequencies for human voices, such as if the user desires to hear other people's voice. In an embodiment, the second low frequency 528 can be 300 Hz. In an embodiment, the second high frequency 530 can be 5 KHz. The second band pass filter can have a more narrow range (difference between the low frequency and high frequency points) than the first band pass filter, such as to concentrate on a more desirable range of frequencies in a louder environment.

FIG. 6 shows a representation of the third band pass filter that can be applied when the level of the sound is above the second threshold. The third band pass filter can filter out frequencies below the third low frequency 632 and above the third high frequency 634. The frequencies between the third low frequency 632 and the third high frequency 634 can include the common frequencies for human voices, such as if the user desires to hear other people's voice. In an embodiment, the third low frequency 632 can be 300 Hz. In an embodiment, the third high frequency 634 can be 3 KHz. The third band pass filter can have a more narrow range (difference between the low frequency and high frequency points) than the second band pass filter, such as to concentrate on a more desirable range of frequencies in a louder environment.

In an embodiment, the plurality of band pass filters that one is selected from can include an emphasis filter, such as a filter that emphasizes high frequencies at the expense of low frequencies (shown in FIG. 6). In an embodiment, the third band pass filter can increase the output level of at least a portion of the frequencies between the third low frequency 632 and the third high frequency 634 compared to the output level of the lower frequencies. As seen in FIG. 6, a portion of the frequencies can be amplified, in an environment with loud background noise, such as to help the user hear the voices (frequencies commonly associated with human voices). In an embodiment, signals at 300 Hz can be decreased by 6-7 dB(A), the signals at 3 KHz can be increased by 6-7 dB(a), and signals at 1 KHz can be unchanged.

The second low frequency can be greater or equal to the first low frequency. The third low frequency can be greater or equal to the second low frequency. The second high frequency can be less than or equal to the first high frequency. The third high frequency can be less than or equal to the second high frequency. The second low frequency and the second high frequency can be within the range of the first low frequency to the first high frequency. The third low frequency and the third high frequency can be within the range of the second low frequency to the second high frequency. It is noted, that a similar pattern could result where the band pass filter being applied is selected from a group of band pass filters including more or less than three band pass filters, such as two band pass filters, four band pass filters, five band pass filters, or six band pass filters. Alternatively, a single variable filter can be included. In various embodiments, a band pass filter can include a high pass filter in series with a low pass filter.

Referring back to FIG. 3, in the example of FIG. 3, the output from the microphone 108 is shown as feeding into the initial band pass filter 326. In one example, an analog-to-digital signal converter (not shown) is present between the microphone 108 and the initial band pass filter 326. The initial band pass filter 326 narrows the frequencies of the signal to eliminate the extreme low end and high end frequencies. In the example of FIG. 3, the output of the band pass filter 326 feeds into both the level digitizer 328 and the Adaptive Frequency Response (AFR) filters 332. The level digitizer 328 outputs the level of the signal to the level processor 330. The level processor 330 determines which of the different band pass filters will be applied and provides that information to the filter module 332. The filter module 332 then applies the specific band pass filter to the signal which was input from the initial band pass filter 326. The filtered signal is then input to the volume control 334. Based on input from the setting of the volume knob controlled by the user, the volume control 334 provides for the appropriate amount of gain by the amplifier 336. Finally, the signal reaches to the speaker 218. Many of the components described as a part of the electronics package 320 can be provided as algorithms running on a microprocessor, including the level digitizer 328, the AFR filters 332, and the level processor 330.

Adaptive Automatic Level Control Decay/Hold/Release Timing

The level and duration of an impulse noise, such as a gunshot, and its echo can be continuously monitored by a second algorithm running on a microprocessor. The second algorithm can analyze the level and duration of the impulse noise and can adjust the length of noise suppression to maximize the reduction of the initial impulse and then reduce the suppression to the lowest level that can mask the impulse noise and its reflections. Suppressing the impulse noise and its reflections can improve an experience for a user, such as when the user is shooting at an indoor range where high impulse noise and reflections are common.

Figure 7:
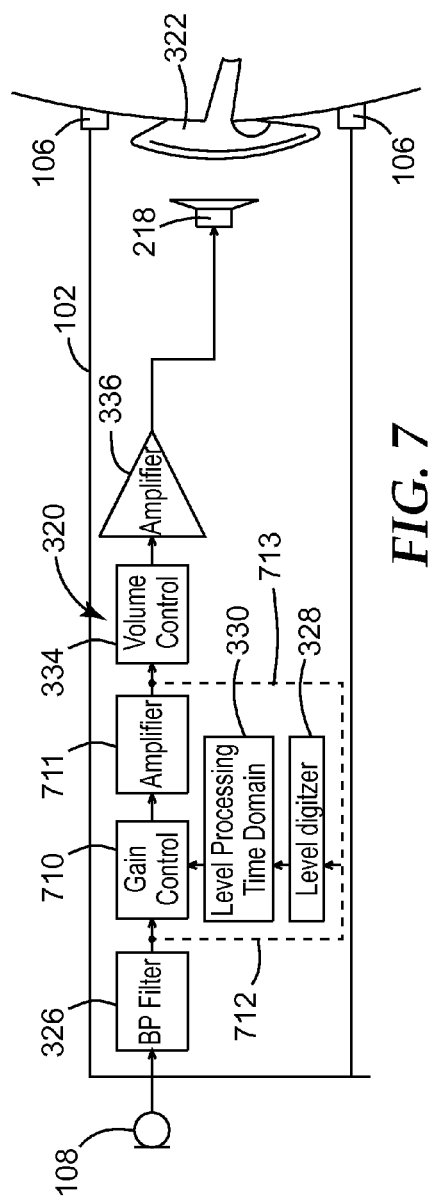
FIG. 7 is a block diagram of a process, according to an embodiment.

Impulse sounds, such as a gunshot can be picked up by the microphone and relayed to the user through the speaker. The electronics package 320 in the headset 100 can apply a second algorithm to the impulse sounds picked up by the microphone. FIG. 7 shows a block diagram of the electronics package 320, according to an embodiment. The electronics package 320 can include an initial band pass filter 326, a level digitizer 328, a level processor 330, a gain controller 710, an amplifier 711, a volume control 334, and an amplifier 336. In an embodiment, the electronics package 320 can include two amplifiers, such as a front end amplifier (not shown) before an analog to digital convertor (also not shown). These two elements can be located between the microphone 108 and the initial band pass filter 326. The electronics package 320 can also include a digital signal processor after the converter. The front end amplifier (not shown) can amplify the sound before it is converted to digital, such as to ensure there is an accurate conversion with the full range of frequencies. In an embodiment, the electronics package 320 can include a feed forward path 712. In an embodiment, the electronics package 320 can include a feedback path 713.

In general, the headset 100 can reduce the amount of sound waves that reach a user's ears, such as by providing a seal around the user ear 322 with the ear cups 102. As discussed above, in some environments a user might desire to hear more of the surrounding environment than the user is able to hear because of the protection provided by the headset 100. The microphone 108 can pick up sounds from the surrounding environment and relay them to a user's ear 322, such as through speaker 218. However, not all of the sounds that are picked up by the microphone are desirable, such as impulse noises. The electronics package 320 can suppress at least some of the impulse noises.

Figure 8:
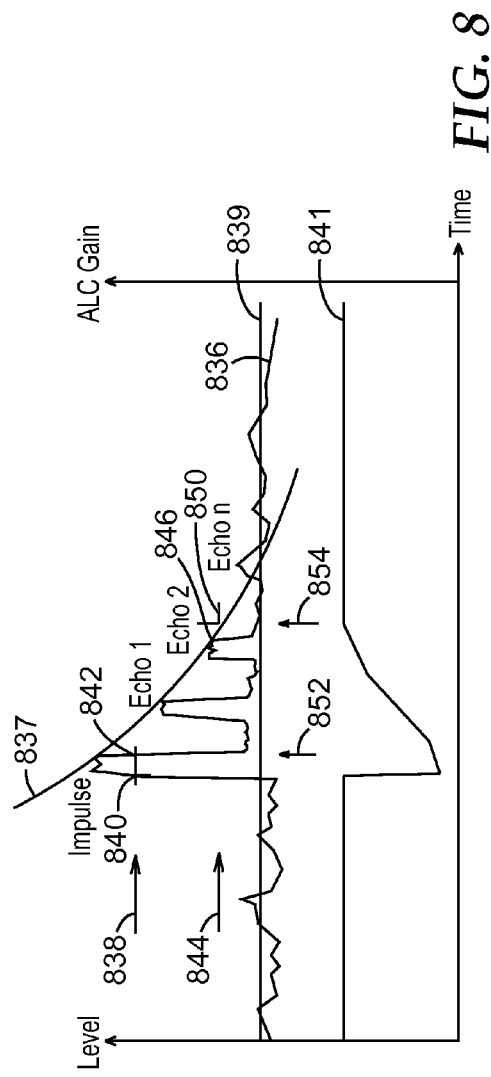
FIG. 8 is a graph of audio filter behavior, according to an embodiment.

The suppression of impulse noises can include two components, (1) the amount of suppression and (2) the amount of time the signal is suppressed. In an embodiment, the amount of suppression can be a standard amount of suppression for all impulse noises, such as if the gain is always set to zero, during the suppression. In an embodiment, the amount of suppression can be dependent upon the level of a previous or first impulse noise during a particular session of use. For example, impulse noises above a first level, but below a second level can result in the subsequent impulse noises having less suppression than an impulse noise above a second level. The amount of suppression can vary throughout the suppression time. For example, there can be more suppression at the beginning of the suppression time when the impulse noise is the loudest and less suppression later in the suppression times when the reflections/echoes are not as loud. FIG. 8 shows a simplified representation of an input 836 of an impulse noise and several echoes of the impulse noise as picked up by the microphone. As seen in FIG. 8, the maximum ALC gain 841 can be affected by the impulse and suppression time. The maximum ALC gain 841 can be gradually increased during the suppression time to match the echo decay rate represented by line 837. In an embodiment, the gain rate of the ALC gain 841 during the suppression time can be in segments, such as 100 millisecond or 50 millisecond segments. In an embodiment, at least some of the segments can be different amounts of time.

The amount of time that the impulse noise is suppressed can vary based on the conditions the headset is being used in. The length of the suppression time can be changed by the electronics package 320, such as at the front end amplifier or the digital signal processor. In an embodiment, the length of time that the impulse is suppressed can be related to what the volume of the speaker is set at, as discussed below in reference to FIGS. 9 and 10. The input 836 can vary based on numerous factors, such as the type of weapon creating the sound and the environment in which the headset is being used (e.g. indoors, outdoors, size of the room, geometry of the room, materials in the room, etc.) Very long shooting ranges will have longer times between echoes, while smaller shooting ranges will have less time between echoes. The angles of the walls will also impact the echo characteristics. When the input 836 reaches the impulse detection threshold 838, the input can be defined as having an impulse noise. In an embodiment, an input noise can be defined as an impulse by the amount of energy of the incoming sound wave. The incoming sound wave has an amplitude and a length of time, thereby defining an amount of energy.

The impulse detection threshold 838 can be set at a level below the saturation level of the microphone. In an embodiment, the saturation level of the microphone can be 130 dB(A) and the impulse detection threshold 838 can be set at 120 dB(A). The level of each echo of the impulse can decay at a rate represented by the line 837. The first echo will be at a lower level than the impulse. Similarly, each of the subsequent echoes can be a lower level, unless an additional impulse is picked up by the microphone.

The microphone can continually pick up background noises. The average background noises can be represented by the average background noise level 839. An impulse can be defined in relation to the average background noise level. In an embodiment, the impulse detection threshold can be 120 dB. In some embodiments the average background noise can be at least 50 dB and no more than 70 dB. In an embodiment, the amount of suppression time can be set at the maximum amount of time when the average background noise is over a designated level, such as 85 dB.

The input 836 reaches the impulse detection threshold 838 at point 840. The input 836 is above the impulse detection threshold 838 until point 842. The time when the impulse is no longer above the impulse detection threshold 838 is referenced by arrow 852. The amount of time between point 840 and point 842 can be measured to determine the level of the impulse noise, even if the microphone is saturated at a point below the level of the impulse noise. The amount of time between point 840 and point 842 is proportional to how loud the impulse noise is, such that a louder impulse noise will have more time between point 840 and point 842 than a quieter impulse noise. In an embodiment, the proportion is assumed to be nonlinear. The echoes or reflections of an impulse noise can also be proportional to the time between point 840 and point 842, such that more time between point 840 and point 842 equates to louder echoes and therefore a longer suppression time is used. In an embodiment, the suppression time can be related to the level of the impulse noise, such that an impulse noise with a higher level necessitates a longer suppression time.

The system can be adaptive, such that it changes the suppression time based on the environment the headset is being used in. For example, a first room can have different reflection characteristics from a second room. In a first room, a suppression time of 250 milliseconds can be sufficient to suppress the impulse noise and its reflections, whereas in a second room a suppression time of 250 milliseconds might not suppress the reflections.

An echo minimum threshold 844 can be set at a level where echoes that peak below the set level are no longer undesirable, such as to define the last echo. The echo minimum threshold 844 can vary based on the average background noise level. In an embodiment, the echo minimum threshold 844 is 15 dB more than the average background noise level 839. Input 836 last crosses the echo minimum threshold 844 at point 846. The time from point 842 to point 846 can be dependent upon the characteristic of the surrounding environment. The suppression time can start at point 840 and end at point 846, such as to include the impulse noise and the reflections of the impulse noise that are above the echo minimum threshold 844. The suppression time can be increased and decreased to more accurately end at point 846, based on analysis of the previous impulse or analysis of the first impulse during a session of use. Line 837, representative of the echo decay rate, can last cross the echo minimum threshold at point 850. The time at which line 837 last crosses the echo minimum threshold can be represented by arrow 854.

The suppression time can be constantly updated, such that if no echo is detected above the echo minimum threshold after the suppression time ends, the suppression time can be decreased. If the suppression time is decreased and still no echo is detected above the echo minimum threshold after the suppression time ends, the suppression time can be further decreased. However, if the suppression time ends and one or more echoes are still detected above the minimum threshold after the suppression time ended, the suppression time can be increased. The last occurrence of the echo minimum threshold being constantly crossed can be constantly monitored, such as to continually update the suppression time.

In an embodiment, the length of the suppression time can be kept unchanged if there is an echo above the minimum echo threshold after half of the suppression time and no echo above the minimum echo threshold after the suppression time. If there is not an echo above the echo minimum threshold after half of the suppression time, the suppression time can be shortened. In an embodiment the suppression time can be shortened such that the new suppression time is equal to the last suppression time minus 75% of the previous suppression time minus the minimum suppression time, e.g. new suppression time=previous suppression time−75% (previous suppression time−minimum suppression time).

If there is an echo after the suppression time, the suppression time can be lengthened. In an embodiment the suppression time can be lengthened, such that the new suppression time is equal to the time of the last echo above the echo minimum threshold.

In an embodiment, the length of the suppression time can be reset to a standard length after the headset is turned OFF. In an embodiment, the length of suppression time can be stored when the headset is turned OFF. When the headset is turned back ON, the length of suppression time can be same as when it was turned OFF and stored. In an embodiment, the length of the first suppression time can be correlated to the volume level set with the knob 110.

Referring back to FIG. 7, in the example of FIG. 7, the output from the microphone 108 is shown as feeding into the initial band pass filter 326. In one example, an analog-to-digital signal converter (not shown) is present between the microphone 108 and the initial band pass filter 326. The initial band pass filter 326 narrows the frequencies of the signal to eliminate the extreme low end and high end frequencies. In the example of FIG. 7, the output of the initial band pass filter 326 feeds into both the level digitizer 328 and the gain control module 710. The level digitizer 328 outputs the level of the signal to the level processor 330. The level processor 330 determines how the gain control should be changed, and provides that information to the gain control module 710. The gain control module 710 applies the specific gain alteration to the signal which was input from the initial band pass filter 326. The altered signal is then input to the volume control 334. Based on input from the setting of the volume knob controlled by the user, the volume control 334 provides for the appropriate amount of gain by the amplifier 336. Finally, the signal reaches to the speaker 218. Many of the components described as a part of the electronics package 320 can be provided as algorithms running on a microprocessor, including the level digitizer 328, the gain control module 710, and the level processor 330.

In an embodiment exemplified in FIGS. 9 and 10, the length of the suppression time can be dependent upon the volume level selected by the user, such as through knob 110. The user can rotate the knob 110 (shown in FIG. 2) to adjust the volume of the output of the speaker. In an embodiment, if the volume is at the lowest possible setting the suppression time can be the shortest. If the volume is at the highest possible setting the suppression time can be the longest. In an embodiment, the shortest suppression time can be 200 milliseconds. In an embodiment, the longest suppression time can be 400 milliseconds. In an embodiment, the longest suppression time can be 800 milliseconds. In an embodiment, the longest suppression time can be 1 second. In an embodiment, the longest suppression time can be 4 seconds. In an embodiment, the suppression time can be from 300 milliseconds to 1 second. In an embodiment, the default suppression time can be 300 milliseconds. Longer and shorter suppression times are possible and may vary based on the surrounding environment.

FIG. 9 shows a block diagram of the electronics package 320, according to an embodiment. The electronics package 320 can include an initial band pass filter 326, a gain controller 910, an amplifier 914, a volume control 918, and an adaptive level control (ALC) module 916. In an embodiment, the electronics package 320 can include two amplifiers or more amplifiers, such as a front end amplifier before an analog to digital convertor, where both of these components are located between the microphone 108 and the initial band pass filter 326. The electronics package 320 can also include a digital signal processor after the converter. In an embodiment, the electronics package 320 can include three amplifiers. A front end amplifier (not shown) can amplify the sound before it is converted to digital, such as to ensure there is an accurate conversion with the full range of frequencies.

FIG. 10 shows a simplified representation of an input 1036 of an impulse noise and several echoes of the impulse noise as picked up by the microphone. As discussed above in reference to FIG. 8, the input 1036 can vary based on numerous factors, such as the type of weapon creating the sound and the environment in which the headset is being used.

When the input 1036 reaches an impulse detection threshold 1038, the input can be defined as having an impulse noise. The level of each echo of the impulse can decay at a rate represented by the line 1037. The first echo will be at a lower level than the impulse. Similarly, each of the subsequent echoes can be a lower level, unless an additional impulse is picked up by the microphone.

The lower part of FIG. 10 shows an example of how maximum gain 1041 can be modified based on the impulse and volume level. The maximum gain 1041 can be gradually increased during the suppression time, such as an estimation of the echo decay rate or to match the echo decay rate represented by line 1037. In an embodiment, the gain rate of the ALC gain 1041 during the suppression time can be in segments, such as 100 millisecond or 50 millisecond segments. In an embodiment, at least some of the segments can have be different amounts of time.

The microphone can continually pick up background noises. The average background noises can be represented by the average background noise level 1039. An impulse can be defined in relation to the average background noise level, similar to as discussed above in reference to FIG. 8. The input 1036 reaches the impulse detection threshold 1038 at point 1040.

FIG. 10 shows the gain for three different volume settings. The gain 1041 can remain constant until an impulse noise is detected, such as an input that surpasses the impulse detection threshold 1038, such as at point 1040. Once an impulse is detected, the gain can be reduced or suppressed. In an embodiment, the amount of suppression can be gradually reduced, such as to gradually return the gain to its normal level over the course of the suppression time. The length of time the gain is suppressed for or the amount of suppression can be dependent on the volume level. As shown in FIG. 10, the portion of the gain 1043 can relate to the volume being low. The portion of the gain 1045 can relate to the volume being medium. The portion of the gain 1047 can relate to the volume being high.

In an embodiment, a higher volume selection results in a longer suppression time. As seen in FIG. 10, the suppression time for the portion of the gain 1045 relating to the volume being medium is longer than the suppression time for the portion of the gain 1043 relating to the volume being low, and shorter than the suppression time for the portion of the gain 1047 relating to the volume being high.

As discussed above, in some scenarios a hearing protection headset will not block or eliminate all sound waves from being heard by the user. Some sound waves can leak through the headset or through portions of the user's head. The user can hear the leakage. In some scenarios, the level of the leakage heard by the user is relatively low, such as compared to what the user would hear without the headset.

The leakage is not processed or filtered through any of the algorithms described herein. As such, a user can hear some levels of leakage. In some scenarios, the leakage can have a higher level than the output from the speaker, such as when the output is suppressed in response to a detection of an impulse noise. In an embodiment, the amount of suppression can be decreased over the suppression time, such that the output level of the speaker is substantially similar to the level of leakage prior to the suppression time ending.

In an embodiment, the decay of the leakage from an impulse noise can be more rapid than the decay in the output of the speaker. In an embodiment, the leakage can have a higher level than the output of the speaker, such as when the output is suppressed. The faster decay of the leakage can result in the level of the leakage reaching the same level as the output of the speaker at a time prior to the suppression ending.

The point at which the level of the leakage is substantially equivalent to the level of the output from the speaker can be a balance point. The balance point can occur more quickly for a low volume selection compared to a high volume selection. Reference line 1070 shows the balance level for a low volume selection. Reference line 1072 shows the balance level for a medium volume selection. Reference line 1074 shows the balance level for a high volume selection.

Referring back to FIG. 9, the example of FIG. 9 has many features and options in common with those described with respect to FIGS. 3 and 7, including the initial band pass filter 326, an analog-to-digital signal converter (not shown) and various amplifiers. In the example of FIG. 9, the output of the initial band pass filter 326 feeds into the gain control module 910, which in turn feeds into an amplifier 914. The amplifier 914 provides a level digitized signal to the ALC module 916. The volume control 918, set by the user, also provides an input to the ALC module 916. The volume control setting provides the decay time control information to the ALC module 916. The ALC module 916 then determines how the gain control should be changed, and provides that information to the gain control module 910. The gain control module 910 applies the specific gain alteration to the signal which was input from the initial band pass filter 326. The altered signal is then input to the amplifier 914 and then to the volume control 918. Based on input from the setting of the volume knob controlled by the user, the volume control 334 provides for the appropriate amount of gain by the amplifier 336. Finally, the signal reaches to the speaker 218. Many of the components described as a part of the electronics package 320 can be provided as algorithms running on a microprocessor, including the ALC module 916 and the gain control module 910.

Handling Radio Communication and Other Intermittent Voice Signals Using Gated ALC for the External Input As discussed above, the headset 100 can include an input connection 112 configured for an external audio device to be coupled to the headset 100, such as to allow a user to hear the output of the external audio device through the speakers 218 in the ear cups 102. The headset 100 can include a sensor that notifies the electronics package 320 when a device is plugged into the input connection 112. When an external audio device is plugged into the input connection 112, the external audio device provides an audio device input signal. In another embodiment, an audio device can be contained within one of the ear cups 102 and can generate an audio device input signal. When an audio device input signal is provided by either of these mechanisms or in another way, a third algorithm can be applied to the audio device input signal from the external audio device. The audio device input signal can be processed by a gated ALC, such as to prevent the ALC (if it was not gated) from being impacted by an input of silence or very low noises. A typical radio communication can include periods of silence and periods of noise (such as voices). If the ALC was not gated, the output of the periods of silence could be undesirably increased, such that when an input of a voice was processed it could be louder than desired.

Figure 11:
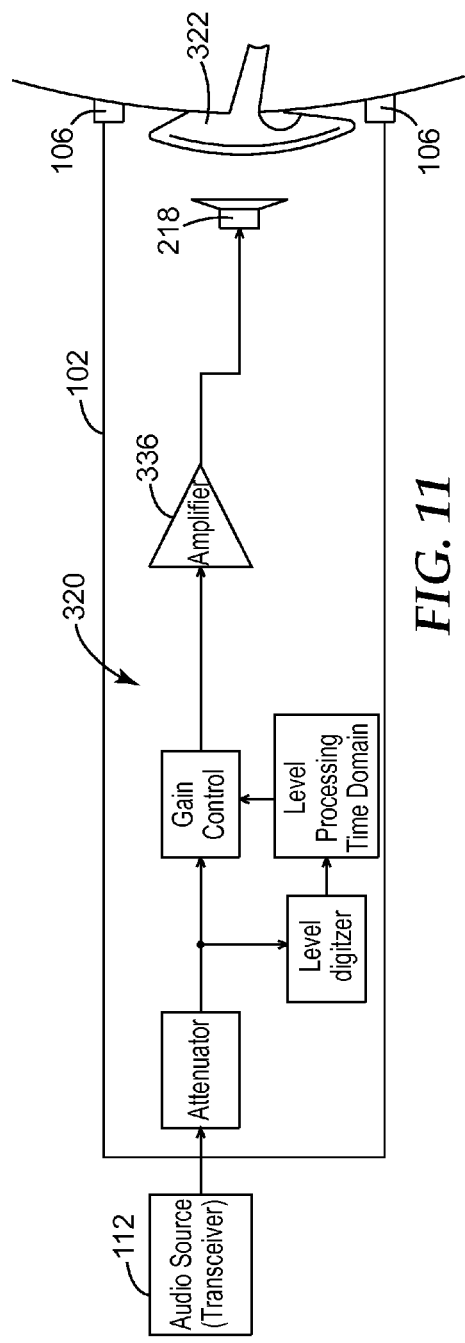
FIG. 11 is a block diagram, according to an embodiment.

FIG. 11 shows a block diagram of the electronics package that can process the audio device input with a gated ALC. The electronics package 320 can include one or more of the following: an attenuator, a level digitizer, a level processor, a gain controller, and an amplifier 336. In an embodiment, the gain controller can be a gated ALC.

Figure 12:
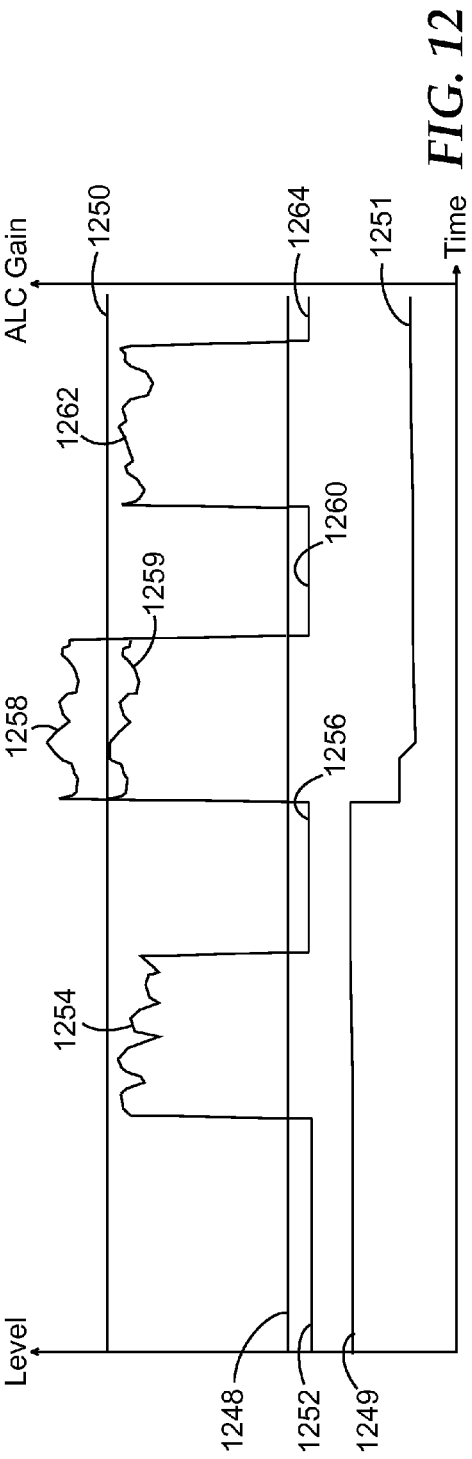
FIG. 12 is a graph of audio filter behavior, according to an embodiment.

The gated ALC can be unaffected by signals below a gate threshold 1248, as seen in FIG. 12. If an audio device input signal is below the gate threshold 1248 it can be ignored by the ALC, such that it will not affect the output of the ALC. The gate threshold 1248 can be set at a low value to ensure that normal music or speech is unaffected by the gating. In an embodiment, the gate threshold 1248 can be set 20 dB below the external input ALC knee level. In an embodiment, the gate threshold 1248 can be set around −40 dBVrms.

An audio device input signal that is below the ALC level 1250 and above the gate threshold level 1248 can cause the ALC gain to slowly increase. In an embodiment, the rate of the ALC gain increases can be 2-3 dB(A)/sec. In an alternative embodiment, the ALC gain increases a set amount over a set amount of time, such as 3 seconds.

Further if a signal is above the ALC level 1250, the signal can be reduced to a level below the ALC level 1250. Reference line 1251 can be representative of the ALC gain. At the start of the input 1249, the ALC gain can be equivalent to the ALC gain from the previous sequence.

To determine if the audio device input signal is below or above the ALC level 1250, an average amplitude of the audio device input signal is determined. The average amplitude can be determined in a number of different ways, including the ways discussed above in relationship to the band pass filter selection process related to the adaptive frequency response feature discussed herein. In an embodiment, the average amplitude is an average of the left and right portions of the audio device input signal. In an embodiment, each portion of the audio device input signal can be root mean squared and then averaged with the root mean squared input from the other side. In an alternative embodiment, input from each side can be averaged and then root mean squared. In an alternative embodiment, the inputs from each side can be combined, such as by setting the output as the maximum of the inputs.

In an embodiment, the average amplitude for determining if the external device audio input is above or below the ALC level can be time averaged, such as to avoid fast changes of gain. In an embodiment, the electronics package 320 can include adding hysteresis, such as to avoid rapidly switching between gain levels even with time averaging.

FIG. 12 shows an audio device input from an audio device, such as a 2-way radio. Other examples of audio devices include radios, MP3 players, CD players and tape players. The audio device input includes portions of silence or low noise 1252, 1256, 1260, 1262. The portions of silence or low noise are not above the gate threshold 1248 and therefore will not affect the gated ALC. The audio device input includes portions of noise, such as voices 1254, 1258, 1262. These portions of noise are at a level above the gate threshold 1248. Portion 1254 and portion 1262 are above the gated threshold and below the ALC level 1250. These portions will be unaffected by the gated ALC, as they are not above the ALC level 1250. Portion 1258 is above the ALC level 1250, and therefore can be reduced to match the ALC level 1250 to prevent the output of the portion 1258 from being too high. Portion 1259 is representative of portion 1258 after it has be reduced, such that it does not exceed the ALC level 1250. The ALC gain will be affected by the portion 1258 above the ALC level 1250, as seen in reference line 1251. In an embodiment, the ALC level 1250 can be set at 82 dB(A), such that sound above 82 dB(A) are suppressed to 82 dB(A).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. An apparatus for hearing protection, comprising:
   a microphone disposed on the apparatus, the microphone configured to pick up an input sound wave from the environment and convert the input sound wave to an incoming signal;
   a processor, configured to apply a band pass filter to the incoming signal to create an output signal;

a speaker disposed on the apparatus, the speaker configured to produce an output using the output signal from the processor;

wherein the band pass filter is adaptively selected by the processor from a plurality of band pass filters, wherein selection of the band pass filter is based on an average amplitude of the incoming sound wave; wherein at least one of the band pass filters for larger amplitudes is more narrowly focused on a selected range of frequencies than at least one of the band pass filters for smaller amplitudes.

2. The apparatus for hearing protection of claim 1, wherein the plurality of band pass filters comprises three different band pass filters.

3. The apparatus for hearing protection of claim 1, wherein the range of frequencies comprises the range of frequencies for human voices.

4. The apparatus according to claim 1, comprising two ear cups, each ear cup defining a cavity configured to fit a user's ear.

5. The apparatus according to claim 4, wherein a speaker is disposed within each cavity defined by the ear cups.

6. The apparatus according to claim 1, comprising a housing containing a speaker configured to fit within a user's outer ear.

7. The apparatus according to claim 2, wherein a first band pass filter is used below a first amplitude threshold, a second band pass filter is used between the first amplitude threshold and a second amplitude threshold, and a third band pass filter is used above the second amplitude threshold.

8. The apparatus according to claim 7, wherein the first amplitude threshold is 65 dB(A) and the second threshold is 80 dB(A).

9. The apparatus according to claim 1, wherein the band pass filter that is applied to the inputs with the largest amplitudes include amplifying at least a portion of the signal.

10. An apparatus for hearing protection, comprising:
a microphone disposed on the apparatus, the microphone configured to pick up an input sound wave from the environment and convert the input sound wave to an incoming signal;
a processor, configured to (1) apply a band pass filter to the incoming signal wherein frequencies of an output signal of the band pass filter vary depending on an amplitude of the incoming signal; and (2) perform one of:
a. suppress an output of the apparatus when the amplitude of the incoming sound signal surpasses an impulse detection threshold; and
b. control the gain of the output using an automatic level controller that applies a constant gain when an audio device input is below a gate threshold, and an adaptive level control (ALC) when the input is above the gate threshold; and a speaker disposed on the apparatus, the speaker configured to produce the output from the processor.

11. The apparatus of claim 10, wherein the step of applying a band pass filter further comprises applying one of a plurality of band pass filters to the input to produce an output; wherein the band pass filter that is applied to the incoming sound wave is selected based on an average amplitude of the incoming sound wave; wherein the band pass filters for larger amplitudes are more narrowly focused on range of frequencies.

12. The apparatus according to claim 10, comprising two ear cups, each ear cup defining a cavity configured to fit a user's ear.

13. The apparatus according to claim 12, wherein a speaker is disposed within each cavity defined by the ear cups.

14. The apparatus according to claim 10, wherein the range of frequencies the plurality of band pass filters includes a range of frequencies for human voices.

15. The apparatus according to claim 10, wherein the plurality of band pass filters comprises three band pass filters.

16. The apparatus according to claim 15, wherein a first band pass filter is used below the first amplitude threshold, a second band pass filter is used between the first amplitude threshold and a second amplitude threshold, and a third band pass filter is used above the second amplitude threshold.

17. The apparatus according to claim 10, wherein the band pass filter that is applied to the inputs with the largest amplitudes amplifies at least a portion of the signal.

18. The apparatus according to claim 10, wherein the processor is configured to suppress the output for a period of time that is at least 200 milliseconds and not longer than 4 seconds.

19. The apparatus according to claim 10, wherein the microprocessor only keeps the gain at a minimum when an external audio device is connected to the apparatus.

20. An apparatus for hearing protection, comprising:
input means for picking up an input sound wave from an environment to create an incoming signal;
selection means for adaptively selecting a band pass filter from a plurality of band pass filters;
application means for applying the selected band pass filter to the incoming signal to create an output; and
output means for converting the output to an output sound wave;
wherein the band pass filter is adaptively selected by the selection means from a plurality of band pass filters based on an average amplitude of the incoming signal; wherein the band pass filters for larger amplitudes are more narrowly focused on a range of frequencies.

* * * * *